US006388150B1

(12) United States Patent
Overbeek et al.

(10) Patent No.: US 6,388,150 B1
(45) Date of Patent: May 14, 2002

(54) SELECTIVE HYDROGENATION PROCESS AND CATALYST THEREFOR

(75) Inventors: Rudolf A. Overbeek, Chatham Township; Robert E. Trubac, Ridgewood; Chiung Yuan Huang, Glen Ridge, all of NJ (US); Marino Rota, Othmarsingen (CH); Nelleke van der Puil, Hoboken, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 0 days.

(21) Appl. No.: 09/483,563

(22) Filed: Jan. 14, 2000

Related U.S. Application Data

(60) Provisional application No. 60/116,649, filed on Jan. 21, 1999.

(51) Int. Cl.⁷ .............................. C07C 7/163; C07C 5/03
(52) U.S. Cl. ........................ 585/260; 585/258; 585/259
(58) Field of Search ................................ 585/258, 259, 585/260, 261

(56) References Cited

U.S. PATENT DOCUMENTS

| | | | | |
|---|---|---|---|---|
| 3,325,556 A | | 6/1967 | DeRosset | 260/677 |
| 3,489,809 A | | 1/1970 | Keith et al. | 260/677 |
| 4,698,324 A | * | 10/1987 | Haruta et al. | 502/243 |
| 5,063,194 A | * | 11/1991 | Broecker et al. | 502/314 |
| 5,080,963 A | | 1/1992 | Tatarchuk et al. | 428/225 |
| 5,096,663 A | | 3/1992 | Tatarchuk | 419/11 |
| 5,102,745 A | | 4/1992 | Tatarchuk et al. | 428/605 |
| 5,187,021 A | * | 2/1993 | Vydra et al. | 428/607 |
| 5,266,546 A | * | 11/1993 | Hearn | 502/300 |
| 5,304,330 A | | 4/1994 | Tatarchuk et al. | 264/61 |
| 5,595,634 A | | 1/1997 | Hearn et al. | 203/29 |
| 5,877,363 A | | 3/1999 | Gildert et al. | 585/260 |
| 6,113,722 A | * | 9/2000 | Hoffmann et al. | 25/68 |
| 6,217,732 B1 | | 4/2001 | Schuh et al. | 204/490 |

FOREIGN PATENT DOCUMENTS

EP 827944 3/1998

* cited by examiner

Primary Examiner—Bekir L. Yildirim
(74) Attorney, Agent, or Firm—Elliot M. Olstein; Raymond J. Lillie

(57) ABSTRACT

A process of selectively hydrogenating an impurity in a feed containing hydrocarbons, such as, for example, an impurity selected from the group consisting of acetylene compounds, dienes, and mixtures thereof in a feed containing at least one monoolefin and the impurity wherein the impurity is hydrogenated selectively in the presence of a selective hydrogenation catalyst supported on a particulate support. The supported catalyst is supported on a mesh-like structure.

30 Claims, No Drawings

SELECTIVE HYDROGENATION PROCESS AND CATALYST THEREFOR

This application claims the priority of U.S. Provisional Application Ser. No. 60/116,649, filed Jan. 21, 1999.

This invention relates to the selective hydrogenation of impurities in a feed containing hydrocarbons. More particularly, this invention relates to a process for selectively hydrogenating compounds having a triple bond as opposed to compounds having any double bond, and/or selectively hydrogenating compounds having two double bonds as opposed to compounds having a single double bond, and/or selectively hydrogenating compounds having a triple bond and compounds having two double bonds as opposed to compounds having a single double bond, and/or selectively hydrogenating compounds that contain cumulated double bonds as opposed to those where the double bonds are separated by one or more single bonds. Such reactions include, but are not limited to, the selective hydrogenation of acetylenic and/or dienic impurities in a feed containing at least one monoolefin, such as, for example, the selective hydrogenation of methylacetylene and propadiene (or MAPD) in a feed containing propylene; the selective hydrogenation of butadiene as opposed to butene; the selective hydrogenation of vinyl and ethyl acetylene and 1,2-butadiene in a feed containing 1,3-butadiene; the selective hydrogenation of acetylene as opposed to ethylene; and the selective hydrogenation of $C_5$ and $C_6$ diolefins as opposed to $C_5$ and $C_6$ monoolefins.

The present invention, in another embodiment, also relates to the selective hydrogenation of olefins and dienes in a stream containing olefins, dienes, and aromatics.

Although the scope of the present invention is not intended to be limited to any specific selective hydrogenation, the invention will be described with particularity with respect to the selective hydrogenation of acetylenic and/or dienic impurities in a feed containing at least one monoolefin.

In the petrochemical industry, there are produced streams which contain one or more monoolefins, and which also contain, as impurities, acetylenic compounds and/or dienes. For example, propylene and/or butene cuts obtained from various pyrolysis processes, particularly pyrolysis in the presence of steam, contain, as impurities, acetylenic compounds and/or dienes, and in general, both acetylenic compounds and dienes. Acetylenic impurities include acetylene, methylacetylene, and diacetylene, and dienic impurities include propadiene, 1,2-butadiene, and 1,3-butadiene. In general, a propylene stream recovered from a steam pyrolysis process contains both methylacetylene and propadiene impurities.

In the petrochemical industry, such a stream is subjected to a selective hydrogenation process in order to hydrogenate the acetylenic and/or dienic impurities, while minimizing hydrogenation of the desired monoolefin. Such a process may be accomplished by a catalytic hydrogenation, using a supported catalyst, such as, for example, a noble metal catalyst, such as a palladium catalyst, supported on a suitable support.

The present invention is directed to an improved method and catalyst for the selective hydrogenation of impurities in a feed containing hydrocarbons.

In accordance with an aspect of the present invention, there is provided a process for selectively hydrogenating one or more impurities in a feed containing hydrocarbons. The process comprises hydrogenating the impurity(ies) in the presence of a selective hydrogenation catalyst supported on a particulate support. The supported catalyst is supported on a mesh-like structure. The term "supported on the mesh" as used herein includes coating the supported catalyst on the mesh as well as entrapping the supported catalyst in the interstices of the mesh. The catalyst that is supported on the mesh, in one embodiment, is comprised of a catalyst supported on a particulate support with the supported catalyst being supported on the mesh. In another embodiment, the catalyst is supported on a particulate support that is supported on one or more other supports that are supported on the mesh.

In one embodiment, the process for selectively hydrogenating an impurity is a process for selectively hydrogenating compounds having a triple bond as opposed to compounds having any double bond and/or selectively hydrogenating compounds having two double bonds as opposed to a single double bond. Representative examples of such selective hydrogenation reactions include, but are not limited to, the selective hydrogenation of acetylenic and/or dienic impurities in a feed containing at least one monoolefin, such as, for example, the selective hydrogenation of methylacetylene and propadiene (MAPD) in a feed containing propylene; the selective hydrogenation of butadiene as opposed to butene; the selective hydrogenation of acetylene as opposed to ethylene; and the selective hydrogenation of $C_5$ and $C_6$ diolefins as opposed to $C_5$ and $C_6$ monoolefins. Other reactions include selectively hydrogenating compounds having a triple bond and those that contain cumulated double bonds as opposed to those where the double bonds are separated by one or more single bonds. In one embodiment, the selective hydrogenation is a process for selectively hydrogenating ethyl and vinyl acetylene and 1,2-butadiene as opposed to 1,3-butadiene.

In one embodiment, the selective hydrogenation is a process for selectively hydrogenating an impurity selected from the group consisting of acetylene compounds, dienes, and mixtures thereof in a feed containing at least one monoolefin and the impurity. The impurity is hydrogenated selectively in the presence of a selective hydrogenation catalyst supported on a particulate support. The supported catalyst is supported on a mesh-like structure.

In another embodiment, the process for selectively hydrogenating an impurity is a process for selectively hydrogenating dienes and styrene in a stream containing dienes, styrene, olefins, and aromatics. An example of such a feed is a pyrolysis gasoline feed. The selective hydrogenation is effected in the presence of a selective hydrogenation catalyst supported on a particulate support, wherein the supported catalyst is supported on a mesh-like structure as described herein.

More particularly, the mesh-like material is comprised of fibers or wires, such as a wire or fiber mesh, a metal felt or gauze, metal fiber filter or the like. The mesh-like structure may be comprised of a single layer, or may include more than one layer of wires; e.g., a knitted wire structure or a woven wire structure and preferably is comprised of a plurality of layers of wires or fibers to form a three dimensional network of materials. In a preferred embodiment, the support structure is comprised of a plurality of layers of fibers that are oriented randomly in the layers. One or more metals may be used in producing a metal mesh Alternatively the mesh fibers may be formed from or include materials other than metals alone or in combination with metals; e.g. carbon or metal oxides or a ceramic. In one embodiment, the mesh includes a metal. In the case where the mesh supports the catalyst, the material which forms the mesh, in one embodiment, is non-catalytic with respect to the selective hydrogenation of impurities in a hydrogenation feed.

In a preferred embodiment wherein the mesh-like structure is comprised of a plurality of layers of fibers to form the three dimensional network of materials, the thickness of such support is at least five microns, and generally does not exceed ten millimeters. In accordance with a preferred embodiment, the thickness of the network is at least 50 microns and more preferably at least 100 microns and generally does not exceed 2 millimeters.

In general, the thickness or diameter of the fibers which form the plurality of layers of fibers is less than about 500 microns, preferably less than about 150 microns and more preferably less than about 30 microns. In a preferred embodiment, the thickness or diameter of the fibers is from about 8 to about 25 microns.

The three dimensional mesh-like structure may be produced as described in U.S. Pat. No. 5,304,330, 5,080,962; 5,102,745 or 5,096,663. It is to be understood, however, that such mesh-like structure may be formed by procedures other than as described in the aforementioned patents.

The mesh-like structure that is employed in the present invention (without supported catalyst on the mesh) has a void volume which is at least 45%, and is preferably at least 55% and is more preferably at least 65% and still more preferably is at least about 90%. In general, the void volume does not exceed about 95% The term "void volume" as used herein is determined by dividing the volume of the structure which is open by the total volume of the structure (openings and mesh material) and multiplying by 100.

Applicants have discovered that when one effects a selective hydrogenation of an impurity(ies) in a feed containing hydrocarbons, in the presence of a selective hydrogenation catalyst, wherein the selective hydrogenation catalyst is supported on a mesh-like structure as hereinabove described, one obtains improved selectivity.

The catalyst which may be employed may be a selective hydrogenation catalyst selected from those known in the art. Such catalysts include, but are not limited to, noble metal catalysts, including palladium, platinum, rhodium, ruthenium and the like, which may or may not include a metal promoter, finely divided copper catalysts, or catalysts containing nickel, silver, or gold. In one embodiment, the catalyst comprises palladium, platinum, silver, nickel, or a combination thereof. In another embodiment, the catalyst has a metal content of from about 0.05% to about 25%. Representative examples of such catalysts are described in U.S. Pat. No. 4,762,956. Such catalysts are supported on a particulate support. Such supports include, but are not limited to, carbon, alumina, 2 aluminum hydroxides, silica, zirconia, titania, kaolin and/or clay compounds, $MgAl_2O_4$, MgO, zeolites, and mixtures thereof The term particulate as used herein includes and encompasses spherical particles, elongated particles, fibers, etc.

In one embodiment, the catalyst is a palladium catalyst which may or may not include a promoter such as a metal promoter. Palladium catalysts which include a promoter include, but are not limited to Pd/Ag catalysts, Pd/Au catalysts, Pd/Cr catalysts, Pd/Pb/$CaCO_3$ catalysts. Alternatively, the palladium catalyst is substantially free of promoters.

In one embodiment, the supported palladium catalyst includes a catalytic amount of palladium supported on an alumina support which is substantially crystalline alpha alumina The supported palladium catalyst may contain a promoter such as silver. The catalyst has an average pore radius of from about 200 Å to 2,000 Å, preferably from 300 Å to 1,500 Å, and more preferably from 300 Å to 600 Å. The pore size distribution is such that at least 80% of the pores have a radius of from 100 Å to 3,000 Å, and preferably from 100 Å to 1,000 Å.

As stated hereinabove, the catalyst has a catalytically effective amount of palladium, with the palladium content generally being at least 0.01 wt. %, and preferably at least 0.1% by weight of the catalyst, and more preferably, from about 0.1 wt. % to about 1.0 wt. % by weight of the catalyst.

The catalyst support generally has a surface area which is no greater than 50 $m^2/g$, and preferably is from 3 $m^2/g$ to 30 $m^2/g$. The porosity of the catalyst in general is from 0.2 to 1.0 ml/g, and preferably is from 0.3 ml/g to 0.6 ml/g. The surface acidity of the catalyst, as measured by adsorption of pyridine at 120° C. and under atmospheric pressure is from 0.002 to 0.05 millimole of pyridine absorbed per gram of catalyst.

The catalyst generally has an active palladium surface area of from 20 to 200 $m^2/g$, and preferably from 40 to 120 $m_2/g$, as measured by oxygen-hydrogen titration. In addition, the palladium is in the form of crystallites having an average size of at least 25 Å and generally no greater than 110 Å.

The alumina support is produced preferably from a mixture of $\beta$-$Al_2O_3$·$3H_2O$, $\alpha$-$Al_2O_3$·$H_2O$, and amorphous aluminum hydroxide, with the $\beta$-$Al_2O_3$·$3H_2O$ being present in the mixture in an amount of from 5% to 35% by weight. Such supported palladium catalysts are described further in U.S. Pat. No. 4,762,956, the contents of which are incorporated herein by reference.

It is to be understood, however, that the scope of the present invention is not to be limited to the specific supported palladium catalysts hereinabove described.

In general, the particulate catalyst support has a surface area of from about 0.1 to about 30 $m_2/g$, preferably from about 1$m^2/g$ to about 200 $m^2/g$, and an average particle size of from about 20 nm to about 300 $\mu$m, preferably from about 0.5 $\mu$m to about 100 $\mu$m. The particulate support preferably has a mean pore diameter of from about 10 nm to about 20 $\mu$m. The catalyst that is supported on the particulate support comprises from about 0.01% to 25%, and preferably from about 0.2% to about 15% of the supported catalyst, based on catalyst and particulate support.

In accordance with another aspect of the present invention, the supported catalyst (catalyst supported on a particulate support) is supported on the mesh-like structure in an amount of at least 5%, and preferably at least 10%, with the amount of supported catalyst generally not exceeding 90% and more generally not exceeding 80%, all by weight, based on mesh and supported catalyst. In one embodiment where the void volume of the mesh-like structure prior to adding supported catalyst is about 90%, the weight percent of supported catalyst is from about 10% to about 50%, and when the void volume is about 95%, the weight percent of supported catalyst is from about 20% to about 90%. In a preferred embodiment, the mesh-like structure that includes supported catalyst is employed in an amount to provide a void volume in the reaction zone of at least 50% and preferably at least 70%. In general, in such a preferred embodiment, the void volume does not exceed about 95%.

It is to be understood that the mesh-like support that supports the supported catalyst may be employed in forms other than hereinabove described. For example, the mesh-like support may be formed as rings, particles, ribbons, etc. and employed in the reactor as a packed bed. In one embodiment, the particle dimensions are smaller than those of packed bed particles that are known in the prior art.

The supported catalyst which is supported on the mesh-like structure may be present on the mesh-like support as a coating on the wires or fibers that form the mesh-like structure and/or may be present and retained in the interstices of the mesh-like structure.

In one embodiment, wherein the catalyst supported on a particulate support is present as a coating on the mesh-like structure, the mesh-like structure may be initially coated with the particulate support, followed by addition of the catalyst to the particulate support present as a coating on the mesh-like structure. Alternatively, the catalyst supported on a particulate support may be coated onto the mesh. In another embodiment, the catalyst supported on a particulate support may be coated onto a particulate support that has been coated onto the mesh-like structure. The particulate support with or without catalyst may be coated on the mesh-like structure by a variety of techniques, e.g., dipping or spraying. After coating the particulate support without catalyst onto the mesh, the support is impregnated with a solution containing the catalyst precursors and is treated thermally to obtain the catalyst.

The supported catalyst particles may be applied to the mesh-like structure by contacting the mesh-like structure with a liquid coating composition (preferably in the form of a coating bath) that includes the particles dispersed in a liquid under conditions such that the coating composition enters or wicks into the mesh-like structure and forms a porous coating on both the interior and exterior portions of the mesh-like structure.

Alternatively, the mesh-like structure is coated with a particulate support containing active catalyst or the mesh-like structure may be coated with particles of a catalyst precursor.

In a preferred embodiment, the liquid coating composition has a kinematic viscosity of no greater than 175 centistrokes and a surface tension of no greater than 300 dynes/cm.

In one embodiment, the supported catalyst or catalyst support is coated onto the mesh by dip-coating. In a preferred embodiment, the three-dimensional mesh-like material is oxidized before coating; e.g., heating in air at a temperature of from 300° C. up to 700° C. In some cases, if the mesh-like material is contaminated with organic material, the mesh-like material is cleaned prior to oxidation; for example, by washing with an organic solvent such as acetone.

The coating bath is preferably a mixed solvent system of organic solvents and water in which the particles are dispersed. The polarity of the solvent system is preferably lower than that of water in order to prevent high solubility of the catalyst and to obtain a good quality slurry for coating. The solvent system may be a mixture of water, amides, esters, and alcohols. The kinematic viscosity of the coating bath is preferably less than 175 centistrokes and the surface tension thereof is preferably less than 300 dynes/cm.

In a preferred embodiment of the invention, the mesh-like structure that is coated includes metal wires or fibers and the metal wires or fibers that are coated are selected or treated in a manner such that the surface tension thereof is higher than 50 dynes/cm, as determined by the method described in *"Advances in Chemistry, 43, Contact Angle, Wettability and Adhesion, American Chemical Society, 1964."*

In coating a mesh-like structure that includes metal fibers, the liquid coating composition preferably has a surface tension from about 50 to 300 dynes/cm, and more preferably from about 50 to 150 dynes/cm, as measured by the capillary tube method, as described in T. C. Patton, "Paint Flow and Pigment Dispersion", $2^{nd}$ Ed., Wiley-Interscience, 1979, p. 223. At the same time, the liquid coating composition has a kinematic viscosity of no greater than 175 centistokes, as measured by a capillary viscometer and described in P.C. Hiemenz, "Principles of colloid and Surface Chemistry", $2^{nd}$ Ed., Marcel Dekker Inc., 1986, p. 182.

In such an embodiment, the surface tension of the metal being coated is coordinated with the viscosity and surface tension of the liquid coating composition such that the liquid coating composition is drawn into the interior of the structure to produce a particulate coating on the mesh-like structure. The metal to be coated preferably has a surface tension which is greater than 50 dynes/cm and preferably is higher than the surface tension of the liquid coating composition to obtain spontaneous wetting and penetration of the liquid into the interior of the mesh.

In the case where the metal of the structure that is to be coated does not have the desired surface tension, the structure may be heat-treated to produce the desired surface tension.

The liquid coating composition can be prepared without any binders or adhesives for causing adherence of the particulate coating to the structure.

The surface of the structure to be coated may also be chemically or physically modified to increase the attraction between the surface and the particles that form the coating; e.g., heat treatment or chemical modification of the surface. The surface of the structure can be modified by coating the non-catalytic support particles to improve attachment.

The solids content of the coating bath generally is from about 2% to about 50%, preferably from about 5% to about 30%.

The bath may also contain additives such as surfactants, dispersants etc. In general, the weight ratio of additives to particles in the coating bath is from 0.0001 to 0.4 and more preferably from 0.001 to 0.1.

The mesh-like material preferably is coated by dipping the mesh-like material into a coating bath one or more times while drying or calcining in between dippings. The temperature of the bath is preferably at room temperature, but has to be sufficiently below the boiling point of the liquid in the bath.

After coating, the mesh-like material that includes a porous coating comprised of a plurality of particles is dried, preferably with the material in a vertical position. The drying is preferably accomplished by contact with a flowing gas (such as air) at a temperature of from 20° C. to 150° C. more preferably from 100° C. to 150° C. After drying, the coated mesh-like material is preferably calcined, for example, at a temperature of from 250° C. to 800° C., preferably 300° C. to 500° C., most preferably at about 400° C. In a preferred embodiment, the temperature and air flow are coordinated in order to produce a drying rate that does not affect adversely the catalyst coating, eg, cracking, blocking of pores, etc. In many cases, a slower rate of drying is preferred.

The thickness of the formed coating may vary. In general, the thickness is at least 1 micron and in general no greater than 100 microns. Typically, the coating thickness does not exceed 50 microns and more typically does not exceed 30 microns.

The interior portion of the mesh material that is coated has a porosity which is sufficient to allow the particles which comprise the coating to penetrate or migrate into the three dimensional network. Thus, the pore size of the three dimensional material and the particle size of the particles comprising the coating, in effect, determine the amount and uniformity of the coating that can be deposited in the interior of the network of material and/or the coating thickness in the network. The larger the pore sizes the greater the thickness of the coating which can be uniformly coated in accordance with the invention.

In the case where the particles are in the form of a catalyst precursor, the product, after the deposit of the particles, is treated to convert the catalyst precursor to an active catalyst. In the case where the particles which are deposited in the three dimensional network of material is a catalyst support, active catalyst or catalyst precursor may then be applied to such support, e.g., by spraying, dipping, or impregnation.

In using a coating bath, the coating bath in some cases may include additives. These additives change the physical characteristics of the coating bath, in particular the viscosity and surface tension such that during dipping penetration of the mesh takes place and a coating can be obtained with a homogeneous distribution on the interior and exterior of the mesh. Sols not only change the physical properties of the coating bath, but also act as binders. After the deposition, the article is dried and calcined.

As representative stabilizing agents there may be mentioned: a polymer like polyacrylic acid, acrylamines, organic quaternary ammonium compounds, or other special mixes which are selected based on the particles. Alternatively an organic solvent can be used for the same purpose. Examples of such solvents are alcohols or liquid paraffins. Control of the pH of the slurry, for example, by addition of $HNO_3$ is another method of changing the viscosity and surface tension of the coating slurry.

In one embodiment, wherein the mesh-like structure is comprised of a plurality of layers of metal fibers, the particulate support with or without catalyst may be coated onto the mesh-like catalyst support by an electrophoretic coating procedure, as described in U.S. application Ser. No. 09/156,023, filed on Sep. 17, 1998. In such a procedure, a wire mesh-like structure is employed as one of the electrodes, and the particulate support, such as an alumina support of the requisite particle size, with or without catalyst, (which preferably also includes alumina in the form of a sol to promote the adherence of larger particles to the wire mesh) is suspended in a coating bath. A potential is applied across the electrodes, one of which is the mesh-like structure formed from a plurality of layers of fibers, and the mesh-like structure is electrophoretically coated with the alumina support with or without catalyst. If the alumina support does not include a catalyst, the catalyst then can be added to the catalyst structure by impregnating with or dipping the structure (which contains the alumina coating) into an appropriate solution that contains the catalyst and possibly one or more promoters.

As hereinabove indicated, the supported catalyst may be supported on the mesh material by entrapping or retaining the particulate support in the interstices of the mesh. For example, in producing a mesh-like structure comprised of a plurality of layers of randomly oriented fibers, the particulate support may be included in the mix that is used for producing the mesh-like structure whereby the mesh-like structure is produced with the particulate support retained in the interstices of the mesh. For example, such mesh-like structure may be produced as described in the aforementioned patents, and with an appropriate support being added to the mesh that contains the fibers and a binder, such as cellulose. The produced mesh structure includes the particulate support retained in the mesh structure. The particulate support retained in the mesh structure then is impregnated with the catalyst precursors and treated thermally to obtain the catalyst.

Alternatively, the selective hydrogenation catalyst hereinabove described may be coated directly onto the mesh, which has been coated with an oxide layer. For example, the mesh may be heated to form an oxide layer. The catalyst then may be applied by chemical vapor deposition or other means. In such an embodiment, the fibers of the mesh preferably have a diameter less than about 30 microns, and more preferably from about 8 microns to about 25 microns. Preferably, the mesh is comprised of a plurality of layers of fibers that are oriented randomly in the layers.

Although the present invention encompasses any reaction involving the selective hydrogenation of impurities in a feed containing hydrocarbons, the invention now will be described with particularity with respect to the selective hydrogenation of acetylenic and/or dienic impurities in a feed containing at least one monoolefin.

In one embodiment, the selective hydrogenation of the acetylenic and/or dienic impurities is effected in a single stage hydrogenation in the presence of the supported catalyst hereinabove described. In one embodiment, the feed is introduced as a liquid and may be partially or completely vaporized during the hydrogenation. In accordance with one embodiment, the hydrogenation is effected in the liquid phase, with no more than 5% of the feed being vaporized during the hydrogenation. It may be advantageous, however, to carry out the reaction with more than 5% of the feed being vaporized.

In such an embodiment, a feed which is to be hydrogenated selectively and a hydrogen-containing gas are introduced into the catalytic hydrogenation reactor at a temperature of from about 0° C. to about 50° C., and the outlet temperature of the catalytic hydrogenation zone generally does not exceed 60° C. The catalytic hydrogenation zone is operated in general at a pressure of from about 14 to about 35 $kg/cm^2$.

Depending upon the level of acetylenic and/or dienic impurities in the feed, the inlet temperature, and the allowable outlet temperature, it may be necessary to recycle a portion of the product to the reaction zone (the recycle is mixed with the feed and hydrogen prior to introduction into the reaction zone).

In general, the recycle ratio (based on fresh feed hydrocarbon), when used, does not exceed 5:1, and preferably does not exceed 3:1; accordingly, the recycle ratio may range from 0:1 to 5:1.

The hydrogen is introduced into the reactor in an amount sufficient to provide for the required selective hydrogenation of the acetylenic and/or dienic impurities, with an increase of the ratio of hydrogen to impurities resulting in a decrease in the selectivity of the hydrogenation. In general, the feed hydrogen-to-impurity mole ratio is determined by the concentration of impurity. The hydrogen may be introduced with a suitable diluent, such as methane.

One or more reactors may be used to remove the impurities, with the hydrogen-to-impurity ratio in the second of two reactors in series being generally greater than that in the first and being determined by the inlet concentration of impurity and being determined by the inlet concentration of impurity to the second reactor.

The selection of a suitable liquid hourly space velocity should be apparent to those skilled in the art. In general, there is obtained an increase in selectivity at higher liquid hourly space velocities.

In one embodiment, wherein a propylene stream, containing methylacetylene and propadiene as impurities, is subjected to selective hydrogenation in accordance with the present invention, such a propylene-containing stream generally contains from about 0.5 to about 5.0 mole percent, and in some cases, even higher amounts, of such impurities.

In some cases, depending on the impurity content of the feed, as well as other factors, the product from the initial selective catalytic hydrogenation may be subjected to a second catalytic hydrogenation. In the case where a second reactor or reaction zone is employed, such second reaction zone is operated generally at a pressure similar to the pressure of the first catalytic hydrogenation stage. The second reactor in general is operated at an inlet temperature in the order of from about 30° C. to about 50° C., and at an outlet temperature not in excess of about 60° C. The second stage in general is operated with a hydrogen-to-impurity mole ratio of from about 3 to about 40 moles of hydrogen-to-mole of impurity, when the first stage preferably is operated with less than 5 wt.% vaporization of the feed.

In another embodiment, the feed containing the impurity is fed as a vapor at a temperature generally between 100° F. and 250° F. The hydrogen-to-impurity mole ratio in the feed generally is between 1.1 and 5.0. One or more reactors may be used.

In another embodiment, the feed containing the impurity is fed to a distillation column where the mesh-like structure containing or coated with catalyst also serves as a distillation packing.

In all of the above-mentioned embodiments, carbon monoxide either may be present in the feed or may be added to the feed as a selectivity promoter. The carbon monoxide may be added either to the hydrogen or hydrocarbon feed.

The invention now will be described with respect to the following examples, however, the scope of the present invention is not intended to be limited thereby.

EXAMPLE 1

A particulate catalyst, and the same catalyst supported on a mesh were used in the selective hydrogenation of methyl acetylene and propadiene in a stream containing propylene. The particulate catalyst is a palladium-silver catalyst on alumina with a surface area of 8 m²/g. The catalyst was supported on the mesh as follows:

The catalyst was ground to a mean particle size of 3μ. A slurry of the particle in water, with 10% solids content, then is made. To this slurry, 0.1 g of a commercially available cationic acrylamide polymer and 0.2 g of a 20% alumina sol (Nyaco™) per 10 g of the supported catalyst were added. The slurry was poured into a bath with two stainless steel electrodes that are connected to the positive pole of a power supply. A mesh sample with a thickness of 0.8 mm, stainless steel fibers of 12μ in diameter and a void volume of 90% was cut to fit the dimensions of the electrodes. The mesh was rinsed with acetone and calcined in air at 300° C. for 1 hour to remove organic contaminants. The mesh was placed at equal distances and parallel to the electrodes, and was connected to the negative pole of the power supply. A potential of 10 volts was applied for 60 seconds, during which the supported catalyst was deposited on the mesh. The coated mesh was removed from the bath and calcined at 500° C. for 1 hour in air. The amount of supported catalyst deposited on the mesh was 22% of the combined weight of the mesh and supported catalyst. The coated mesh was cut into strips of approximately 5 mm by 10 mm. The catalysts were loaded into the reactor between α-Al₂O₃ beads of 1 mm and glass wool.

The activities of the palladium-silver extrudates and the same catalyst as a coating on the mesh were measured in the selective hydrogenation of methylacetylene arid propadiene in a stream containing propylene. The feed to the reactor, which was a 0.75 inch outer diameter (od) tube, consisted of:

0.78 wt. %–0.84 wt. % methyl acetylene
0.32 wt. %–0.33 wt. % propadiene
21.3 wt. %–23.5 wt. % propylene dissolved hydrogen H₂/(MA+PD) molar ratio=0.75–0.83 balance-isobutane The selective hydrogenation was conducted at an LHSV of 367 to 369 hr⁻¹.

At the end of the reaction, propadiene conversion (%) and selectivity (%) were measured for the reaction in the presence of the particulate catalyst alone and the same catalyst supported on a mesh. Selectivity is defined as:

propylene made/(methyl acetylene+propadiene converted)×100.

The results are given in Table I below.

TABLE I

| catalyst support | Temp. (° C.) | Pressure (psig) | H₂(MA + PD) | propadiene conversion (%) | selectivity (%) |
| --- | --- | --- | --- | --- | --- |
| mesh | 56 | 415 | 0.75 | 34.6 | 88 2 |
| extrudates | 49 | 400 | 0.83 | 29.2 | 71.4 |

EXAMPLE 2

A selective hydrogenation catalyst containing Pd and Ag on an inert support was ground in an Eiger ball mill for fifteen minutes at 4000 rpm to make a slurry of 25 weight percent solids to produce a mean particle size of 1.5 micron. To this slurry mixture 1 weight % of Nyacol alumina sol was added on the basis of the solids weight in the slurry and the slurry was diluted to 17.3%. A 0.8 millimeter thick stainless steel sheet containing 12 micron fibers with a porosity of 90% was cut, corrugated and formed into 16 different sheet sizes. The different sheet sizes then were coated with this slurry mixture by dip coating of the individual sheets. The excess slurry on the sheets was removed by shaking and dipping on a paper towel. The sheets then were dried at 120° C. for 15 minutes. After drying the sheets were stacked bundle-wise for a heat treatment in air at 500° C. A total of 22 bundles were made with the average percentage of catalyst on the coated bundles being 14.4%. These bundles were loaded into a fixed bed reactor and successfully used for the selective hydrogenation of MAPD in the gas phase.

EXAMPLE 3

A selective hydrogenation catalyst containing Pd and Ag on an inert support was ground in an Eiger ball mill for fifteen minutes at 4000 rpm to make a slurry of 21 weight percent solids to produce a mean particle size of 1.5 micron. To this slurry mixture 1 weight % of Nyacol alumina sol was added on the basis of the solids weight in the slurry and the slurry was diluted to 10%. A stainless steel sheet made of 12 micron fibers, 0.8 millimeter thick with a porosity of 90% was cut, corrugated and rolled together with a flat sheet into a monolith, 17 mm outer diameter and 45 mm length. A total of 22 monoliths were made. The different monoliths were then coated with this slurry mixture by dip coating of the individual monoliths. The excess slurry on the sheet was removed via an air knife. The monoliths were then dried at 120° C. for 20 minutes and treated in air at 500° C. for 1 hour. A total of 22 monoliths were made with the average percentage of catalyst on the coated monoliths being 8.63%. These monoliths were loaded into a fixed bed reactor and successfully used for the selective liquid phase hydrogenation of 1,3 butadiene.

The disclosures of all patents and publications referenced in this specification are specifically incorporated herein by reference in their entirety to the same extent as if each such individual patent and publication were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A process for selectively hydrogenating an impurity in a feed containing hydrocarbons, comprising:
   selectively hydrogenating said impurity in the presence of a selective hydrogenation catalyst supported on a particulate support, said supported catalyst being supported on a mesh structure, said mesh structure being a three-dimensional network formed of a plurality of layers of fibers that are oriented randomly in the layers.

2. The process of claim 1 wherein said fibers have a diameter of less than 30 microns.

3. The process of claim 2 wherein said fibers have a diameter of from about 8 microns to about 25 microns.

4. The process of claim 1 wherein said impurity is selected from the group consisting of acetylene compounds, dienes, and mixtures thereof, and said feed contains at least one monoolefin and said impurity.

5. The process of claim 1 wherein said impurity is selected from the group consisting of olefins and dienes, and said feed contains at least one impurity and one aromatic compound.

6. The process of claim 1 wherein said impurity is selected from the group consisting of acetylenes and a compound containing adjacent double bonds, and said feed includes a compound containing double bonds separated by at least one single bond.

7. The process of claim 1 wherein said feed further includes carbon monoxide.

8. The process of claim 1 wherein the particulate support has a surface area of from about 0.1 $m^2/g$ to about 300 $m^2/g$.

9. The process of claim 8 wherein the particulate support has a surface area of from about 1 $m^2/g$ to about 200 $m^2/g$.

10. The process of claim 1 wherein said supported catalyst comprises palladium, platinum, silver, nickel, or a combination thereof.

11. The process of claim 10 wherein said supported catalyst has a metal content of from about 0.05% to about 25%.

12. The process of claim 1 wherein said mesh has a void volume which is at least 45%.

13. The process of claim 12 wherein said mesh has a void volume which is at least 55%.

14. The process of claim 13 wherein said mesh has a void volume which is at least 65%.

15. The process of claim 14 wherein said mesh has a void volume which is at least 90%.

16. The process of claim 13 wherein said mesh has a void volume which does not exceed 95%.

17. The process of claim 1 wherein the supported catalyst is coated on said mesh structure.

18. The process of claim 1 wherein the supported catalyst is entrapped in the interstices of said mesh structure.

19. A process for selectively hydrogenating an impurity in a feed containing hydrocarbons, comprising:
    selectively hydrogenating said impurity in the presence of a selective hydrogenation catalyst, said catalyst being coated onto a mesh structure, said mesh structure being a three-dimensional network formed of plurality of layers of fibers that are oriented randomly in the layers.

20. The process of claim 19 wherein said fibers have a diameter of less than 30 microns.

21. The process of claim 20 wherein said fibers have a diameter of from about 8 microns to about 25 microns.

22. The process of claim 19 wherein said impurity is selected from the group consisting of acetylene compounds, dienes, and mixtures thereof, and said feed contains at least one monoolefin and said impurity.

23. The process of claim 19 wherein said impurity is selected from the group consisting of olefins and dienes, and said feed contains at least one impurity and one aromatic compound.

24. The process of claim 19 wherein said impurity is selected from the group consisting of acetylenes and a compound containing adjacent double bonds, and said feed includes a compound containing double bonds separated by at least one single bond.

25. The process of claim 19 wherein said feed further includes carbon monoxide.

26. The process of claim 19 wherein said mesh has a void volume which is at least 45%.

27. The process of claim 26 wherein said mesh has a void volume which is at least 55%.

28. The process of claim 27 wherein said mesh has a void volume which is at least 65%.

29. The process of claim 28 wherein said mesh has a void volume which is at least 90%.

30. The process of claim 29 wherein said mesh has a void volume which does not exceed 95%.

\* \* \* \* \*